United States Patent
Jansen et al.

(10) Patent No.: US 8,552,389 B2
(45) Date of Patent: Oct. 8, 2013

(54) SYSTEM AND METHOD FOR COLLIMATION IN DIAGNOSTIC IMAGING SYSTEMS

(75) Inventors: Floribertus P. M. Heukensfeldt Jansen, Ballston Lake, NY (US); Yaron Hefetz, Kibbutz alonim (IL)

(73) Assignee: General Electric Company, Niskayuna, NY (US)

( * ) Notice: Subject to any disclaimer, the term of this patent is extended or adjusted under 35 U.S.C. 154(b) by 207 days.

(21) Appl. No.: 12/915,873

(22) Filed: Oct. 29, 2010

(65) Prior Publication Data

US 2012/0108948 A1    May 3, 2012

(51) Int. Cl.
*G21K 1/02*    (2006.01)

(52) U.S. Cl.
USPC ..................................... 250/363.1

(58) Field of Classification Search
USPC ..................................... 250/363.1
See application file for complete search history.

(56) References Cited

U.S. PATENT DOCUMENTS

| | | | |
|---|---|---|---|
| 4,748,328 A | 5/1988 | Chang et al. | |
| 5,638,817 A | 6/1997 | Morgan et al. | |
| 6,242,743 B1 * | 6/2001 | DeVito et al. | 250/363.05 |
| 6,271,524 B1 | 8/2001 | Wainer et al. | |
| 7,339,174 B1 | 3/2008 | Hugg et al. | |
| 7,470,907 B2 | 12/2008 | Hugg et al. | |
| 7,683,333 B2 | 3/2010 | Wieczorek | |
| 7,705,316 B2 | 4/2010 | Rousso et al. | |
| 2007/0221853 A1 * | 9/2007 | Joung | 250/363.09 |
| 2008/0011954 A1 | 1/2008 | Hefetz | |
| 2011/0163235 A1 * | 7/2011 | Soluri et al. | 250/361 R |

OTHER PUBLICATIONS

Bal et al., "Cardiac Imaging Using a Four-Segment Slant-Hole Collimator", IEEE Transactions on Nuclear Science, vol. 53, Issue 5, pp. 2619-2627, Oct. 2006.

Holmberg et al., "Collimator Design and Manufacturing for a Mobile Tomographic Gamma Camera System Based on Ectomography", IEEE Nuclear Science Symposium and Medical Imaging Conference Record, vol. 3, pp. 1571-1574, Oct. 21-28, 1995, San Francisco, CA, USA.

Metzler et al., "Slit-Slat and Multi-Slit-Slat Collimator Design and Experimentally Acquired Phantom Images From a Rotating Prototype", IEEE Transactions on Nuclear Science, vol. 57, Issue 1, pp. 125-134, Feb. 2010.

Tsui et al., "Improved Myocardial Perfusion Spect using a Rotational Multi-segment Slant-hole Collimator", The Journal of Nuclear Medicine, vol. 48(supplement 2), pp. 161, May 2007.

* cited by examiner

*Primary Examiner* — David Porta
*Assistant Examiner* — Hugh H Maupin
(74) *Attorney, Agent, or Firm* — Scott J. Asmus

(57) ABSTRACT

A system and method for collimation in diagnostic imaging systems is provided. One collimation system includes a collimator for a radiation imaging detector having a plurality of adjustable segments and a plurality of collimator holes within each of the plurality of adjustable segments. The plurality of adjustable segments are configured to move independently of a detector to adjust a field of view of the collimator holes.

20 Claims, 10 Drawing Sheets

SYSTEM AND METHOD FOR COLLIMATION IN DIAGNOSTIC IMAGING SYSTEMS

BACKGROUND OF THE INVENTION

This subject matter disclosed herein relates generally to diagnostic imaging systems, and more particularly to detector collimation in Nuclear Medicine (NM) imaging systems.

In NM imaging, radiopharmaceuticals are taken internally and then detectors (e.g., gamma cameras), typically mounted on a gantry, capture and form images from the radiation emitted by the radiopharmaceuticals. The NM images primarily show physiological function of, for example, a patient or a portion of a patient being imaged.

In some types of scans, such as when scanning the whole body or with large patients, the portion of the patient being imaged may require the entire field of view of a conventional large size imaging detector. However, when imaging a structure that is smaller than the field of view of the imaging detector, such as the heart, liver, kidney, brain, breast or a tumor, portions of the imaging detector will acquire patient data outside of the structure of interest. Therefore, an effective sensitivity is decreased that is unrelated to collimator geometrical sensitivity, but results from the opportunity lost by not collecting useful information.

Collimation may be used to focus the field of view. In particular, a converging collimator can be used to improve the sensitivity of the detector over a limited field of view. For example, conventional converging fan beam collimators may be used wherein the lines of responses converge along a line. However, because the focal line is beyond the region of interest, the imaging volume decreases with decreasing distance to the focus such that objects of interest may be outside of the field of view and not imaged. Thus, multiple image scans may need to be performed or different types of collimators may be needed for different scans.

BRIEF DESCRIPTION OF THE INVENTION

In accordance with an embodiment, a collimator for a radiation imaging detector is provided that includes a plurality of adjustable segments and a plurality of collimator holes within each of the plurality of adjustable segments. The plurality of adjustable segments are configured to move independently of a detector to adjust a field of view of the collimator holes.

In accordance with another embodiment, a nuclear medicine (NM) imaging system is provided that includes a gantry and at least one imaging detector supported on the gantry configured to rotate about the gantry defining an axis of rotation. The NM imaging system further includes a segmented collimator connected to the at least one imaging detector, wherein the segmented collimator has a plurality of movable segments configured to move independently of the at least one imaging detector such that the movable segments are independently controllable. The NM imaging system also includes a controller configured to control movement of the movable segments.

In accordance with yet another embodiment, a method for collimating a detector of an imaging system is provided. The method includes configuring a segmented collimator to provide movement of each of a plurality of segments independently of a detector to adjust a field of view of collimator holes of the plurality of segments and coupling the segmented collimator to the detector of the imaging system. The method further includes providing a controller to control the imaging system to move at least one of the plurality of segments, the detector or a gantry of the imaging system to which the detector is coupled.

DETAILED DESCRIPTION OF THE INVENTION

Figure 1:
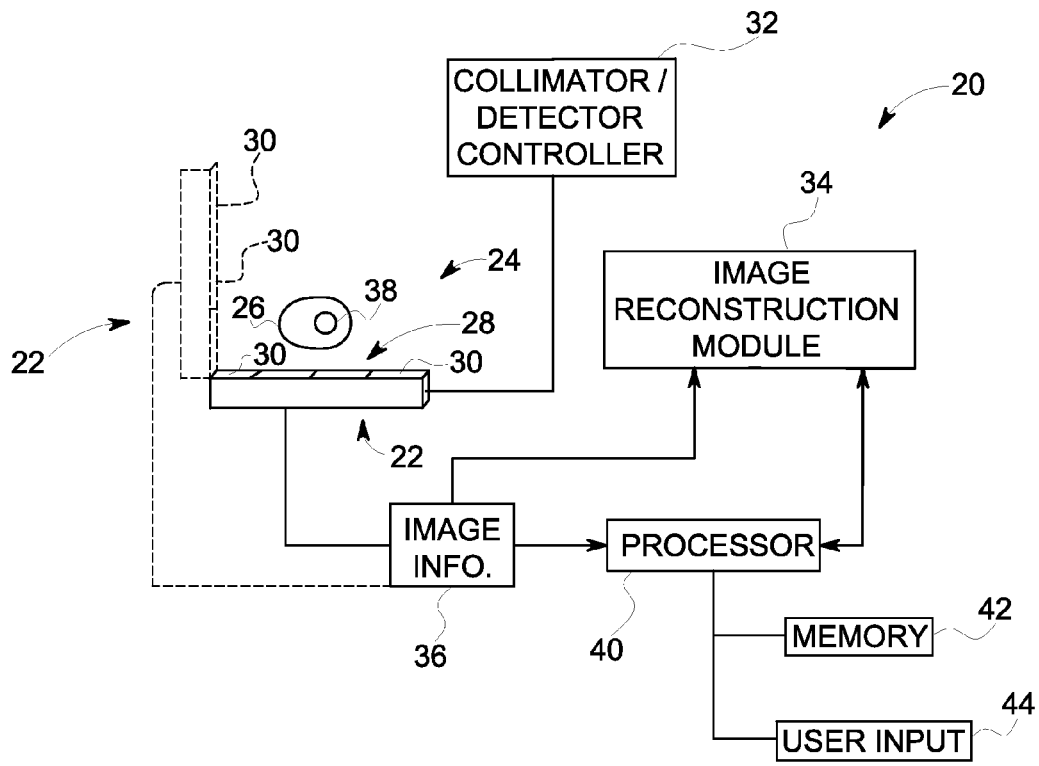
FIG. 1 is a schematic block diagram illustrating a Nuclear Medicine (NM) imaging system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a system and method for collimation in diagnostic imaging systems, such as a Nuclear Medicine (NM) imaging system. For example, a collimator arrangement may be provided for use in a Single Photon Emission Computed Tomography (SPECT) imaging system. The collimator arrangement is adaptive or dynamic such that the field of view is adjustable for different patients and organs to be imaged. By practicing at least one embodiment, and at least one technical effect is that enhanced or optimized imaging can be provided. Additionally, by practicing at least one embodiment, a conventional Sodium Iodide (NaI) SPECT camera can be used for organ specific imaging with improved performance.

Some embodiments provide a segmented parallel-hole collimator that includes adjustable collimator segments. For example, the collimator segments are adjustable to swivel about an axis parallel to the axis of rotation of the detectors of the SPECT system. Alternatively, collimator segments may swivel about an axis normal to the axis of rotation of the detectors of the SPECT system. An NM imaging system 20 may be provided as illustrated in FIG. 1 having an NM camera configured as a SPECT detector 22. It should be noted that the various embodiments are not limited to the NM imaging system 20 having a single detector 22 operable to perform SPECT imaging. For example, the NM imaging system 20 optionally may include one or more additional detectors 22 (an additional detector 22 is illustrated in dashed lines) such that a pair of detectors 22 is provided having a central opening 24 therethrough. An object, such as a patient 26, is positioned in proximity to the one or more detectors 22 for imaging.

It should be noted that number of detectors 22 may be greater than two, for example three or more. In a multi-detector camera, the position of the detectors 22 may be substantially at 90 degrees to each other as illustrated in FIG. 1, or in different configurations as known in the art. It also should be noted that in a multi-detector camera configuration, some of the collimators may optionally be a standard collimator, for example a parallel hole collimator or a standard fan-beam collimator, or a cone-beam collimator, while at least one of the collimators is a segmented collimator according to one or more of the various embodiments. Alternatively, all of the collimators may be segmented collimators according to one or more of the various embodiments.

The detectors 22 may be pixelated detectors that may operate, for example, in an event counting mode. The pixelated detectors 22 may be configured to acquire SPECT image data. The detectors 22 may be formed from different materials, particularly semiconductor materials, such as cadmium zinc telluride (CdZnTe), often referred to as CZT, cadmium telluride (CdTe), and silicon (Si), among others. In some embodiments, a plurality of detector modules are provided, each having a plurality of pixels. In other embodiments, the detector 22 may be made of a scintillation crystal such as NaI coupled to an array of Photo-Multiplier Tubes (PMTs). However, it should be noted that the various embodiments are not limited to a particular type or configuration of detectors, and any suitable imaging detector may be used.

The detectors 22 are fitted with (e.g., have coupled thereto) collimators 28 that include a plurality of adjustable segments 30, which may be adjusted independently, in groups or all together. For example, four adjustable segments 30 are illustrated that define four independently and individually movable portions that can be used to adjust the field of view of the respective detector 22 as described in more detail herein.

The detectors 22 may be provided in different configurations, for example, in single planar imaging mode (illustrated in FIG. 1), a two detector 22 "L" mode configuration (illustrated in FIG. 1 with the dashed line detector 22), an "H" mode configuration, or a three headed camera, among others. Additionally, a gantry (not shown) supporting the detectors 22 may be configured in different shapes, for example, as a "C" and the detectors 22 may be arranged in different configurations, for example, in an "H" or "L" arrangement.

The imaging system 20 also includes a collimator/detector controller 32 that operates to control the movement of the collimators 28 and/or the detectors 22. For example, the collimator/detector controller 32 may control movement of the detectors 22, such as to rotate the detectors 22 around a patient, and which may also include moving the detectors closer or farther from the patient 26 and pivoting the detectors 22. The collimator/detector controller 32 may also control the movement of the adjustable segments 30 of the collimators 28, such that the segments 30 are moved individually or in groups. Thus, the collimator/detector controller 32 may also control movement of each of the segments 30, separate from the movement of the entire collimator 28. For example, the collimator/detector controller 32 may control pivoting movement of the segments 30 or the entire collimator 28.

It should be noted that the collimator/detector controller 32 may be a single unit controlling movement of both the collimators 28 and the detectors 22, or may be separate units.

The imaging system 20 also includes an image reconstruction module 34 configured to generate images from acquired image information 36 received from the detectors 22. For example, the image reconstruction module 34 may operate using NM image reconstruction techniques, such as SPECT image reconstruction techniques to generate SPECT images of the patient 26, which may include an object of interest, such as the heart 38 of the patient.

In some embodiments, the reconstruction of the image information 36 is performed using an appropriate system matrix in an iterative reconstruction calculation. In an exemplary embodiment, the reconstruction process treats data from every strip/detector/gantry angle combination as a separate projection, and computes the probability of image voxels being "seen" by this combination. These determined probabilities are then used to perform an iterative reconstruction, such as using a SPECT iterative construction method. Other methods of reconstructing complex datasets of emission imaging also may be used. For example, reconstruction methods disclosed in U.S. Published Patent Application 20080011954A1 entitled "Apparatus and methods for processing imaging data from multiple detectors", and other references disclosed therein may be used for reconstruction of data acquired by the various embodiments.

Variations and modifications to the various embodiments are contemplated. For example, in a dual headed system, namely one with two detectors 22, one detector 22 may include the collimator 28 with the movable segments 30 while the other detector 22 includes a parallel hole collimator with non-moving segments or a single segment. In this embodiment, the detector 22 with the non-moving parallel hole collimator can obtain information for the entire FOV, while the detector 22 with the collimator 28 with the movable segments 30 focuses on a smaller region of interest (ROI) to provide higher quality information (e.g., more accurate photon counting). Accordingly, the collimator 28 with the movable segments 30 provides a virtual fanbeam that can focus on a smaller ROI.

The image reconstruction module 34 may be implemented in connection with or on a processor 40 (e.g., workstation) that is coupled to the imaging system 20. Optionally, the image reconstruction module 34 may be implemented as a module or device that is coupled to or installed in the processor 40.

The image information 36 received by the processor 40 may be stored for a short term (e.g., during processing) or for a long term (e.g., for later offline retrieval) in a memory 42. The memory 42 may be any type of data storage device, which may also store databases of information. The memory 42 may be separate from or form part of the processor 40. A user input 44, which may include a user interface selection device, such as a computer mouse, trackball and/or keyboard is also provided to receive a user input, such as to change a position of the movable segments 30.

Thus, during operation, the output from the detectors 22, which may include the image information 36, such as projection data from a plurality of segment/detector/gantry angles is transmitted to the processor 40 and the image reconstruction module 34 for reconstruction and formation of one or more images.

Figure 2:
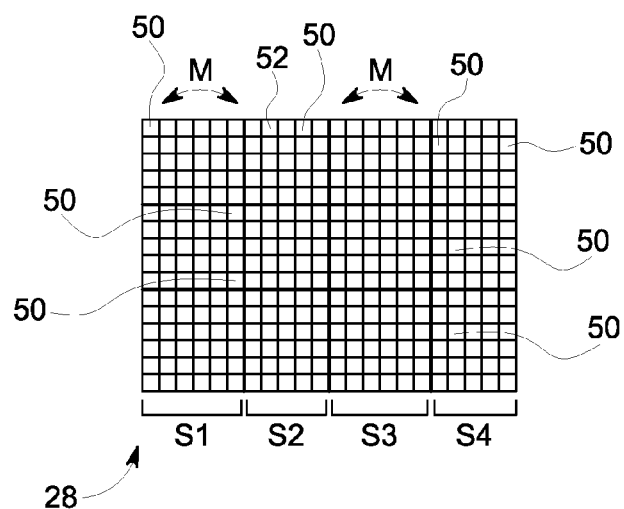
FIG. 2 is a diagram of a collimator formed in accordance with various embodiments.
Figure 3:
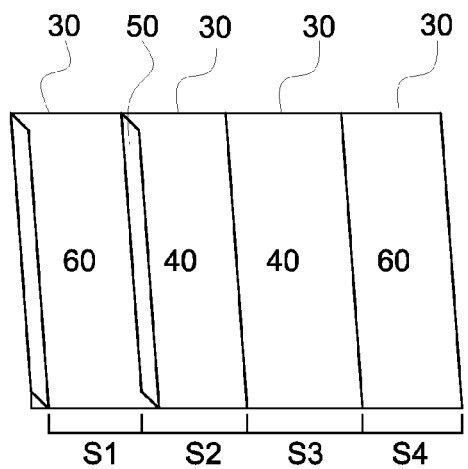
FIG. 3 is a diagram illustrating different tilt angles of a collimator formed in accordance with various embodiments.

As illustrated in FIG. 2, the collimator 28 may include four adjustable segments 30 ($S_1$-$S_4$), with each being movable. The movement of the segments 30 may include swiveling movement as illustrated by the M arrows. In some embodiments, the movable segments 30 move independently or together or in sub-groups. Moreover, the angle of the holes 50 in each of the segments 30 may be different with each directed towards a ROI. However, two or more of the segments 30 may have segments 30 angled inwardly (toward the middle of the detector 22) to the same degree. For example, segments $S_1$ and $S_4$ may be angled the same while segments $S_2$ and $S_3$ are angled the same, such as six degrees and four degrees, respectively, as illustrated in FIG. 3. Thus, the holes 50 may define different projection angles in the different segments 30. It should be noted that the rectangular shape of the holes 50 in FIG. 2 is for illustration only, and other shapes, for example hexagonal or round collimator bores may be used. Additionally, it should be noted that the segments 30 need not be shaped as strips and may be arranged in a two-dimensional configuration. For example, a 3×3 array of 9 segments 30 may be used. Further, some segments 30 may be wedge shaped, have a curved outline, or may be provided in different shapes.

It should be noted that the segments 30 and holes 50 may be formed from any suitable collimator material, for example, lead or tungsten. It also should be noted that different segments 30 may be formed having different parameters such as bore size, shape, angulations and length.

Figure 4:
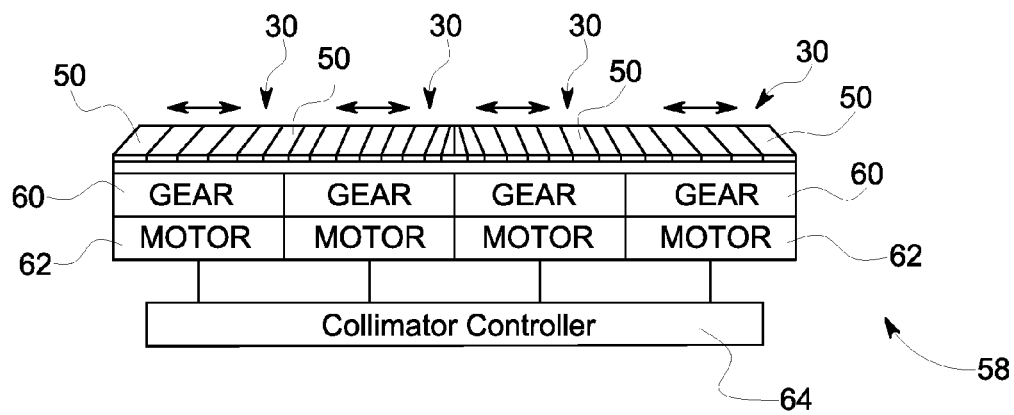
FIG. 4 is a block diagram of a drive arrangement formed in accordance with various embodiments.

The segments 30 may be moved using any suitable driving mechanism such that the segments 30 move either independently or together to adjust the field of view of the detector 22. For example, as illustrated in FIG. 4, a drive arrangement 58 having a gear arrangement 60 may be provided in connection with each of the segments 30. Each gear arrangement 60 may be separately powered by a corresponding motor 62 (as illustrated) or optionally by a single common motor. The motor 62 and gear arrangement 60 are controlled by a collimator controller 64, which may form part of the collimator/detector controller 32. Thus, in various embodiments, the movement of the segments 30 may be driven by one or more motors 62 via the gear arrangements 60, which may be, for example, a rack/pinion, belt, screw and nut, or crankshaft/drive gear arrangement, among others. The segments 30 may swivel (e.g., pivot) about a pivot axis, with the pivot axis for each of the plurality of segments 30 being parallel.

It should be noted that although the holes 50 are illustrated as defining generally parallel holes 52, namely openings through the collimator 28, the various embodiments are not limited to parallel hole 52 arrangements. For example, the holes 50 may define a fanbeam arrangement wherein the holes 52 are not parallel, but have a different relative angle and/or different focal lengths. Additionally, the holes 52 in some embodiments may have a degree of pre-slanting or may be perpendicular to the surface of the detector 22. For example, in the pre-slanting arrangements, the holes 50 may be slanted such that the holes 50 are pre-focused to a typical point of offset. Thus, the collimator 28 formed in accordance with various embodiments may have different configurations. The collimator 28, thus, may define one of a parallel, slant, diverging fanbeam or converging fanbeam arrangement, among others. In some embodiments, the holes 50 define a slant-hole collimator 28.

Modifications and variations are contemplated to the various embodiments. For example, each of the segments 30 may different sizes of holes 52. In some embodiments, the holes 50 that are usually further from the ROI (near the edge of the detector 22) may be longer holes to compensate for the greater distance to the ROI (at the expense of sensitivity, but maintaining some resolution). In other embodiments, the segments 30 may be converging or diverging along the axis rotation of the imaging system 20 (shown in FIG. 1), which effectively reduces or increases, respectively, the FOV in the direction along the axis of rotation and increases the sensitivity. When the FOV is known to be quite small (e.g., in the heart) this additional convergence can provide additional improvement in sensitivity. In still other embodiments, the holes 50 in each of the segments 30 may be angled different from one segment 30 to another along the short or long axis of the segment 30.

Figure 5:
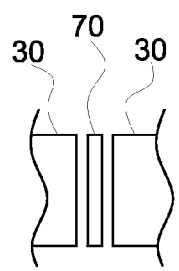
FIG. 5 is a diagram illustrating a shielding arrangement in accordance with various embodiments.
Figure 6:
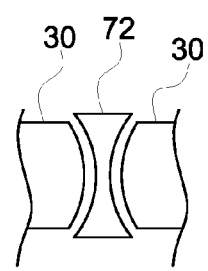
FIG. 6 is a diagram illustrating another shielding arrangement in accordance with various embodiments.

Shielding also may be provided in the region between the collimator segments 30 (or behind the segments) to reduce or prevent high count rates caused by radiation penetrating through the gap between adjacent segments 30. As illustrated in FIG. 5, a generally planar shielding member 70 may be provided between adjacent segments 30. In some embodiments, the collimator segments 30 have curved or rounded ends as shown in FIG. 6 to provide for motion of the segments 30. In this embodiment, a complementary shielding member 72 is provided between adjacent segments 30. For example, the ends of the segments 30 may be convex, while the shielding member 72 has a concave middle portion in an hour-glass shape or configuration. It should be noted that the amount of spacing between the segments 30 may be varied based on the amount of rotation desired or needed for the segments 30. It also should be noted that the shielding members 70 and 72 may be formed from any type of collimator or photon blocking material, such as lead or tungsten. In embodiments wherein one or more of the segments 30 are stationary, the shielding members 70 and/or 72 may be removed or not provided and the segments 30 configured to fit closely or snugly to (e.g., abut) each other, to reduce or minimize radiation leaks. Alternatively, radiation leaks may be reduced or prevented by applying a material with a high stopping power such as an epoxy glue mixed with lead or tungsten powder.

In operation, each of the segments 30 and the corresponding holes 50 may be in a fixed position for the entire exam, with only the detector 22 (or detectors 22) moving around (rotating around) the patient 26 (both shown in FIG. 1). In other embodiments, the segments 30 may move to a new position for every detector position, such as to keep the FOV "in focus". In still other embodiments, the segments 30 may move to multiple positions for each position of the detector so as to "sweep" a larger area of the FOV.

Thus, the segments 30 can swivel or rotate through an angle range, for example, +/−10 degrees, which allows the FOV to move. The amount of movement of the FOV may be changed based on the amount of angular motion provided and the distance from the collimator 28 to the FOV. Using the various embodiments, both the size and location of the FOV may be changed. Additionally, the detectors 22 may be tilted to provide an additional level of adjustment.

Image data may be acquired by one or more different movements in accordance with various embodiments. For example, collimator swivel, detector tilt and/or gantry rotation may be used separately or in combination in accordance with various embodiments. It should be noted that the positioning of the segments 30 can be automatic based on prior information (e.g., CT information), emission information (adapting during the scan), atlas-based information (e.g., all hearts are roughly in a particular location), user interaction (e.g., concentration defined at a particular location), information based on the reconstructed image (another form of adaptive), among other information or factors. In some exemplary embodiments, the direction of at least one of the segments 30 is dynamically adjusted during data acquisition based on the acquired data. In some embodiments, segment direction may be automatically adjusted such that the FOV defined by the segment 30 is centered on an organ-of-interest (OOI). For example, segment direction may be adjusted to increase or maximize the count rate in the FOV defined by the segment 30. In some embodiments, the segment 30 may perform slow undulation to determine the angle of highest count rate. Alternatively, image processing methods or software may be used for determining the center of the OOI and to aim the segment 30 towards the OOI. In other embodiments, a 3D image may be reconstructed using partial data acquired during part of the acquisition. The location of the OOI is determined from the reconstruction and is used for aiming at least some of the segments 30 thereafter, which may be used, for example, in a multi-rotation imaging.

Figure 7:
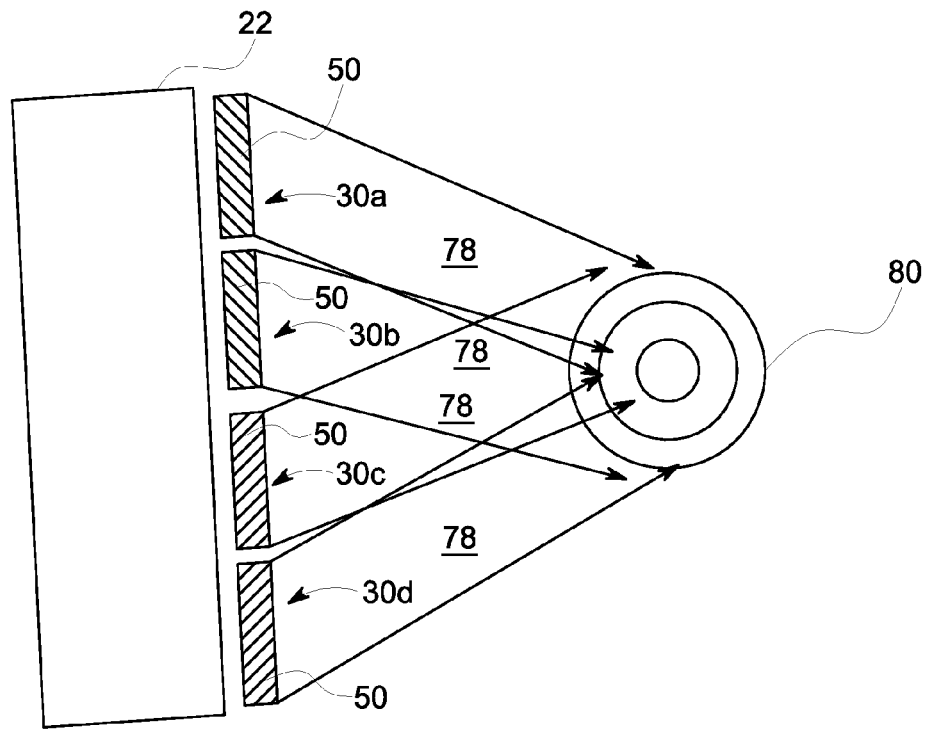
FIG. 7 is a diagram illustrating collimator movement in accordance with one embodiment.

Different types of movement will now be described. As shown in FIG. 7, each of the segments 30 is stationary and generally parallel to the front surface of the detector 22. In this embodiment, each segment 30 may be independently swiveled (e.g., rotated or pivoted) to focus the FOV 78 of each on an ROI 80. The holes 50 in different ones of the segments 30 may be angled differently such that each set of holes 50 corresponding to different segments 30 are focused on the ROI 80 by tilting each set of segments 30 differently. It should be noted that at least two sets of the different segments 30 (e.g., segments 30a and 28d, and 28b and 28c) may be tilted the same amount.

Figure 8:
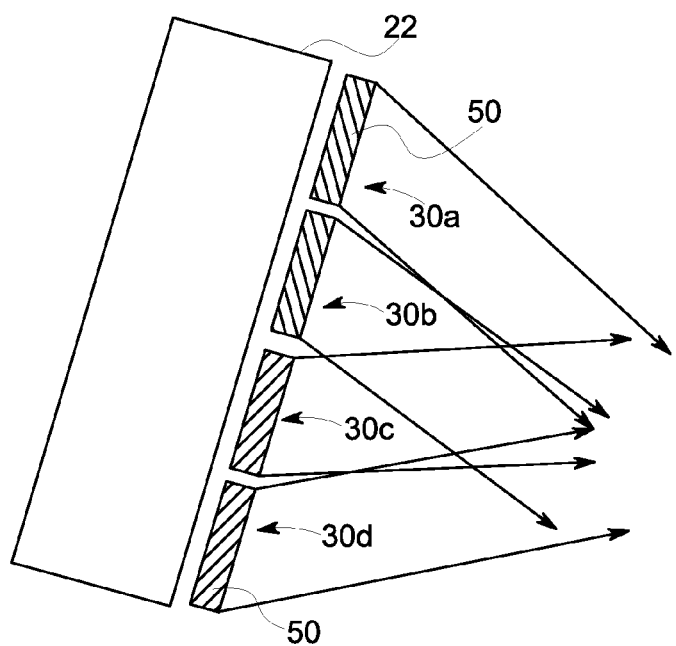
FIG. 8 is a diagram illustrating detector movement in accordance with one embodiment.

As another example, the detector 22 may be tilted as shown in FIG. 8. In this embodiment, the holes 50 of the segments 30 may also be angled as described above. The detector 22 is tilted, for example, relative to an axis of rotation such that a different portion of the ROI may be imaged and not just the center of rotation. The detector 22 may be tilted using any suitable drive mechanism and as described in more detail herein.

Figure 9:
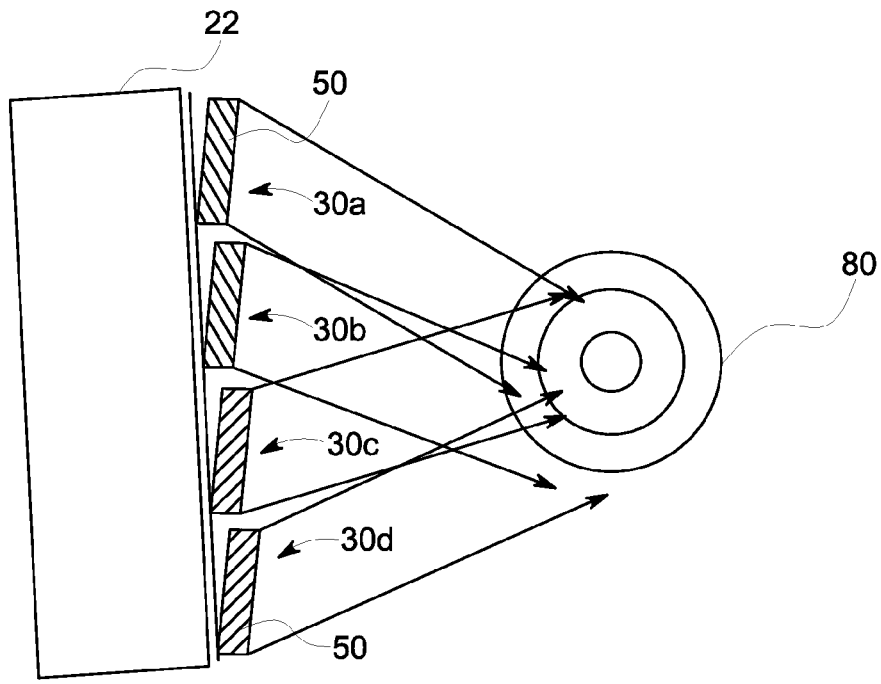
FIG. 9 is a diagram illustrating collimator movement in accordance with another embodiment.

As still another example, the individual segments 30 may be tilted. For example, as illustrated in FIG. 9, one or more of the segments 30 may be tilted such that the segments are no longer parallel to the front surface of the detector. In this embodiment, the holes 50 of the segments 30 may also be angled as described above. The segments 30 may be tilted using any suitable drive mechanism and as described in more detail herein. It should be noted that although the axis of rotation of each of the segments 30 is illustrated at a middle of the each of the segments 30, the axis of rotation may be changed for one or more of the segments 30. For example, axis of rotation can be offset, particularly at the end segments 30, such that the segments 30 rotate about a point closer to an end, such as an inner end (closer to the middle of the detector 22) of the segment 30. Using this segment swivel movement, the sensitivity may cover or "paint" a larger area of the FOV such that image data is acquired from a larger overall region.

Figure 10:
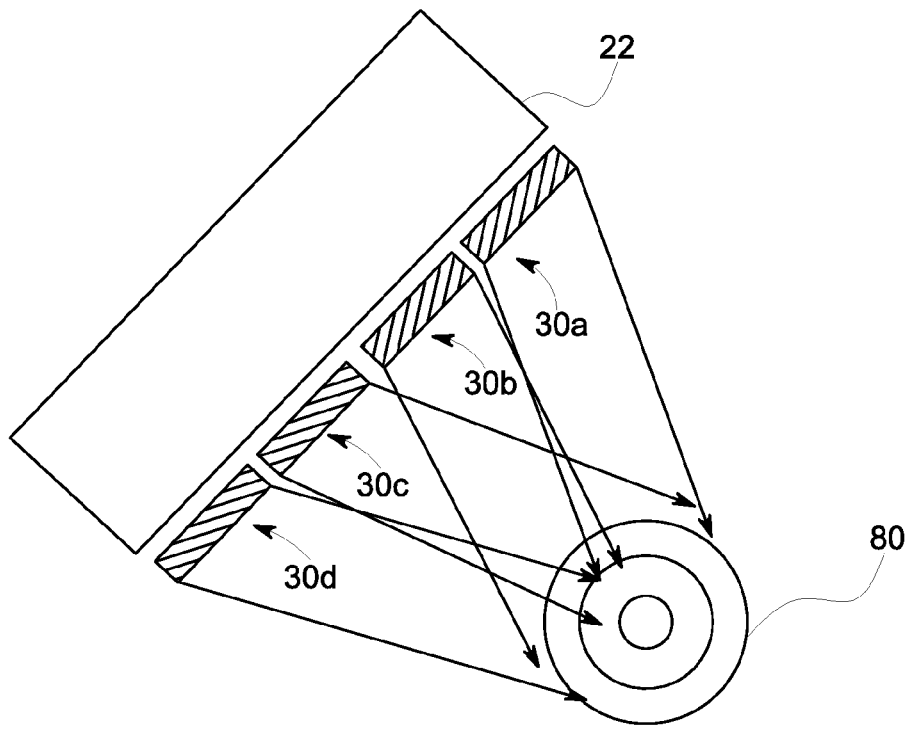
FIG. 10 is a diagram illustrating detector movement in accordance with another embodiment.

As yet another example, the detector 22 may be moved as illustrated in FIG. 10. For example, the detector may rotate around a gantry (not shown) and about the ROI 80 (such as rotated relative to the gantry position illustrated in FIG. 8). Again, in this embodiment, the holes 50 of the segments 30 may also be angled as described above.

It should be noted the one movement is not exclusive of other movements. Accordingly, one or more of the movements described herein may be performed simultaneously, concurrently, consecutively, or otherwise.

Figure 11:
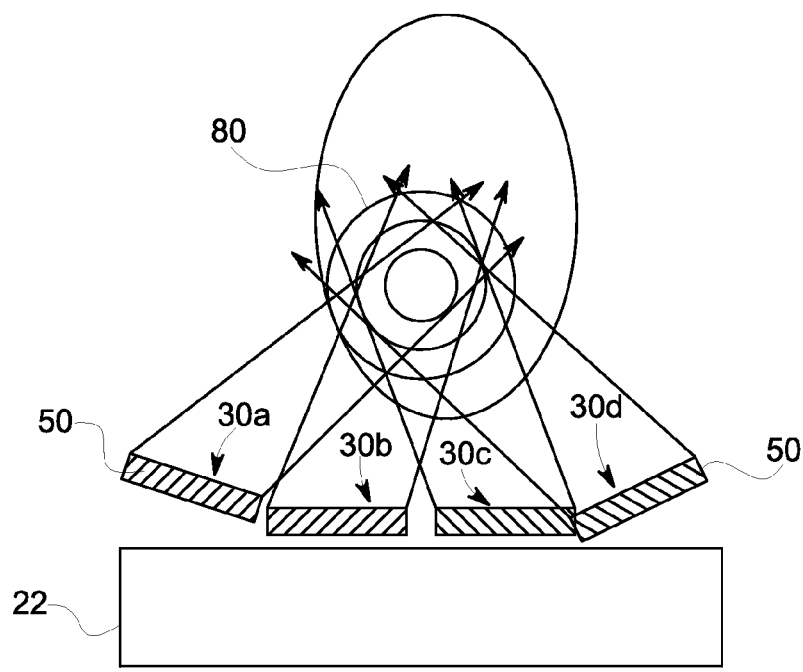
FIG. 11 is a diagram illustrating collimator movement in accordance with another embodiment for a near field of view.
Figure 12:
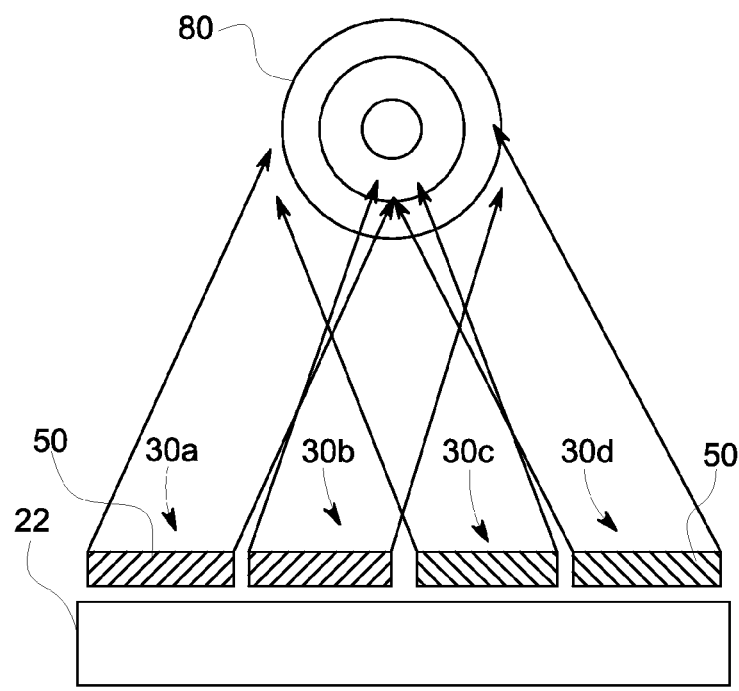
FIG. 12 is a diagram illustrating collimator movement in accordance with another embodiment for a far field of view.

Accordingly, as shown in FIG. 11, each of the segments 50 (and also the holes 50 of each segment 30) may be provided at different angles to provide a near FOV. A far FOV may be provided as shown in FIG. 12, wherein the segments 30 are not tilted and are parallel to the front surface of the detector 22. It should be noted that an even farther FOV may be provided if the segments 30 are outwardly tilted (opposite to the direction indicated in FIG. 11).

Figure 13:
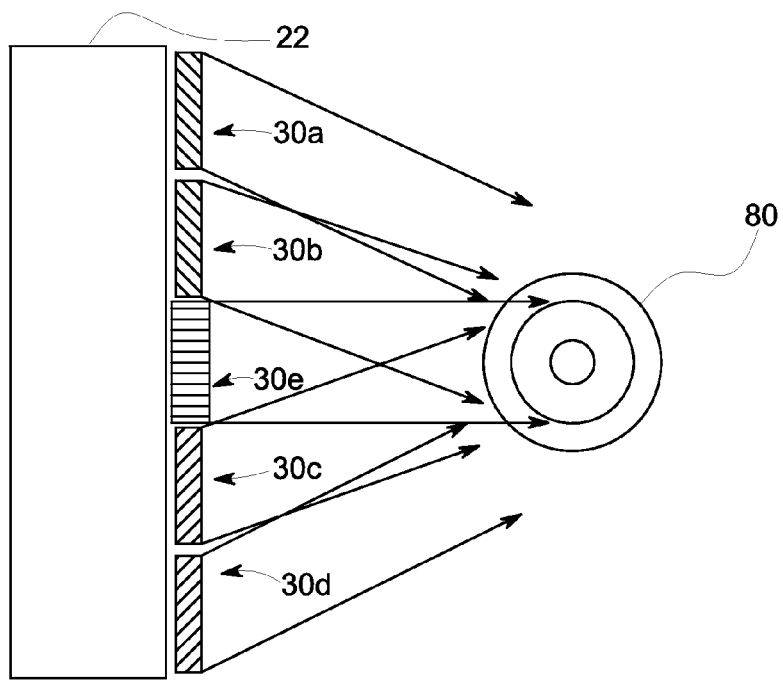
FIG. 13 is a diagram illustrating a collimator formed in accordance with another embodiment.

It should be noted that although an even number of segments 30 are illustrated, namely four, a different number, such as an odd number of segments may be provided. For example, as shown in FIG. 13, five segments 30a-e may be provided. In this embodiment, the center segment 30e may have a parallel hole positioning or arrangement with no slant, while the outer segments 30a-d have holes 50 that are angled as described herein.

Figure 14:
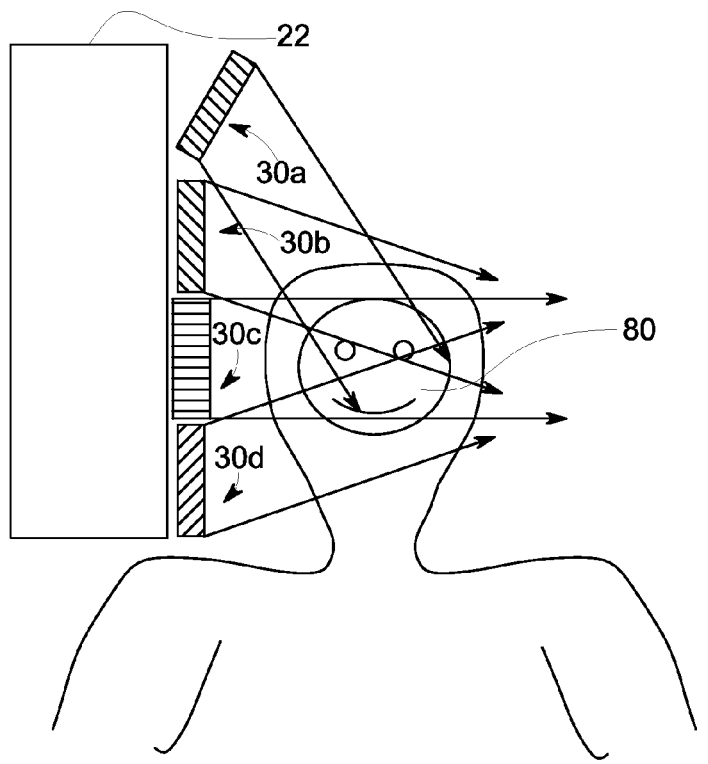
FIG. 14 is a diagram illustrating collimator movement in accordance with another embodiment.

Other variations and modifications may be provided, such as moving some, but not all of the segments 30. For example, as shown in FIG. 14, only one segment 30a may be tilted relative to the front surface of the detector 22, with the other segments 30b-d remaining parallel to the front face. In this embodiment, the holes 50 of the segments 30 may also be angled as described above. Thus, an asymmetric arrangement may be provided, which may be used for brain imaging. A dedicated collimator also may be constructed with asymmetric fixed segment angulations for specific imaging applications such as brain imaging.

In operation, prior to acquiring or during acquiring an image of a structure of interest, the detector(s) 22, collimators 28, segments 30 and/or other members may be adjusted to focus the FOV on a structure or object of interest. Additionally, a patient table or gantry also may be moved. With a collimator with fixed segments, the patient table may be moved during acquisition such that the OOI is adequately or sufficiently imaged by the plurality of segments. Image data is then acquired by each of the detectors 22, which may be combined and reconstructed into a composite image that may comprise two-dimensional (2D) images, a three-dimensional (3D) volume or a 3D volume over time (4D).

Figure 15:
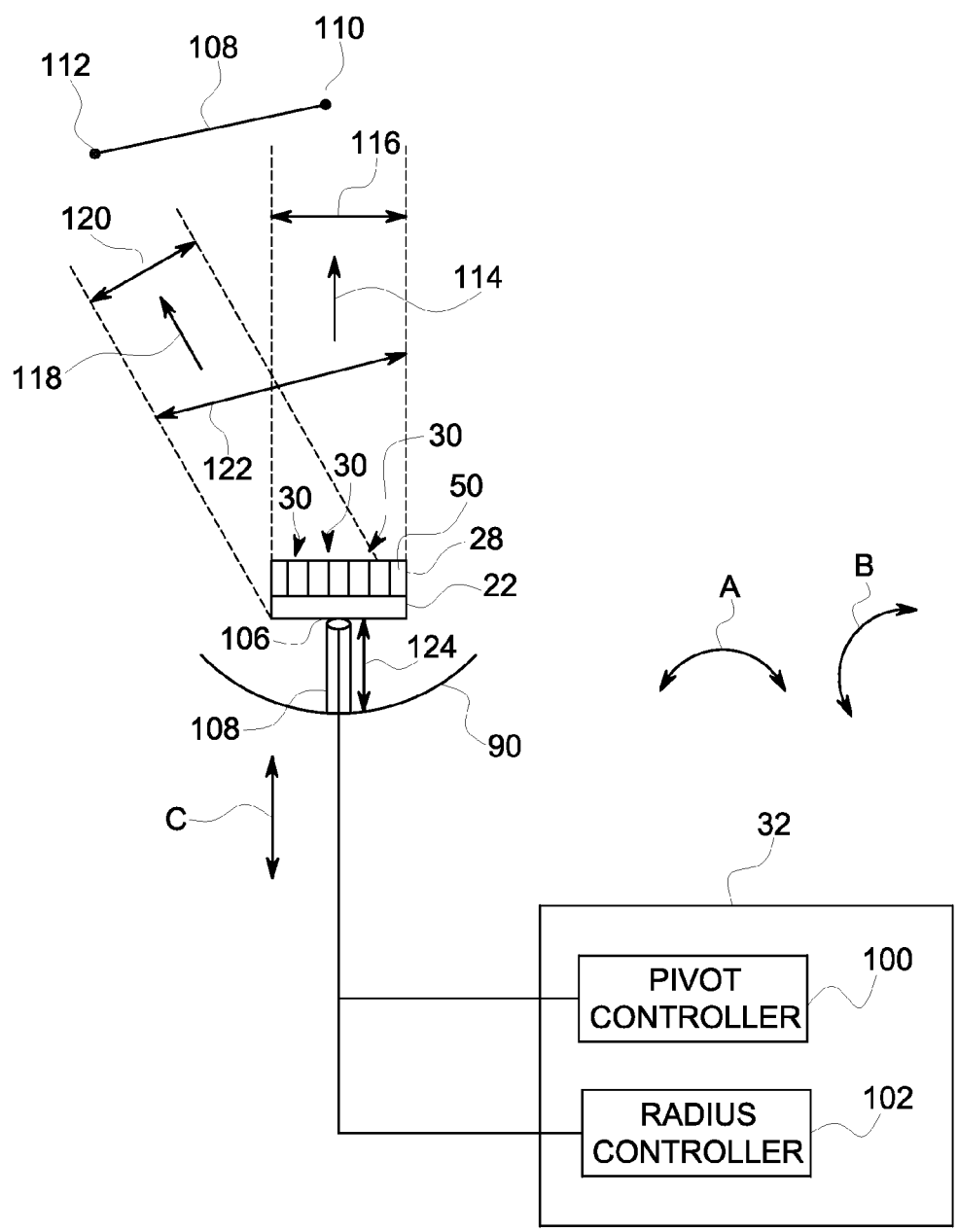
FIG. 15 is a diagram illustrating a drive arrangement for moving detectors formed in accordance with various embodiments.

In addition to the collimator movement, the detectors 22 may be moved to also adjust the effective field of view for one or more of the detectors 22, such that the FOV is reoriented or decreased/increased, such as by pivoting one or more of the detectors 22, translating one or more of the detectors 22 and/or adjusting one or more of the collimators 28 as described herein. Referring specifically to FIG. 15, movement of one of the detectors 22 is illustrated, for example, to change the direction from which the respective detecting face of the detectors 22 senses gamma emissions or radiation separate from the movement of the collimator 28. It should be noted that in this embodiment, the collimator 28 may move as described in more detail herein.

The one or more detectors 22 may be mounted on a pivot 106 that is at the end of a support member 108 (e.g., a leg) mounted to a support structure 90 of an image detector, for example, of a gamma detector. Other pivoting mechanisms may be used. In this embodiment, the collimator/detector controller 32 includes a pivot controller 100 that can command the pivot 106 to move along arrow A, along arrow B (which is orthogonal to arrow A), or any position between the arrows A and B. The pivoting motion may be used together with one or more of the other movements as described herein.

A pivot range 108 for each of the detectors 22 may be provided. For example, when imaging a structure that is larger than the actual FOV of the detectors 22 or to focus on a different object, the pivot range 108 may have a start point 110 at one end wherein the FOV images one outer edge of the structure or is pointed toward a particular object. Optionally, a predefined amount of surrounding tissue may be imaged. An end point 112 of the pivot range 108 may be set to image an opposite outer edge of the structure as well as a predefined amount of surrounding tissue. Therefore, a pivot range 108 may be defined for each of the detectors 22 that may be specific to a particular scan.

Alternatively, one or more of the detectors 22 may be moved through a fixed, predetermined pivot range 108. A rate or speed of pivoting may also be predetermined, set by an operator, or determined based on the anatomy being scanned, size of the structure, level of radiation detected, and the like. It should be noted that rate of pivoting need not be constant throughout the pivot range 108, may be different for a different axis of pivoting, and may be different for different imaging detectors or throughout the duration of the acquisition. For example, the rate of pivoting may be higher during parts of the pivoting range 108 wherein the detectors 22 are aimed at the surrounding tissue. Thus, the detectors 22 collect more data from the structure of interest than from the surrounding tissue.

It should be noted that the pivoting operation can take the form of a series of angular steps, wherein either the step size or the time per step (or both) can be changed to change the rate of pivoting. Additionally, alternative motion can be continuous (but with variable speed) in which case a frequent readout of the actual position of the collimator (e.g., every millisecond or every time an event is detected) is provided and the information about the collimator location is communicated along with the event for subsequent processing.

Moreover, the detectors 22 may remain focused on a particular area or may be adjusted or moved. For example, the detectors 22 may acquire image data at a first position 114 corresponding to the start point 110 of the pivot range 108. The actual FOV 116 of the detectors 22 is dependent in part upon the adjustment of the collimator 28 as described herein. The detectors 22 are pivoted through the pivot range 108 along the direction of arrow A to a second position 118 corresponding to the end point 112 with an actual FOV 120. An effective FOV 122 that is larger than either of the actual FOVs 116 and 120 is formed. The detectors 22 may continuously acquire data while pivoting from the first position 114 to the second position 118. Alternatively, the detectors 22 may acquire a series of images as the pivot controller 100 moves the detectors 22 through the pivot range 108. Alternatively, the pivot controller 100 may move the detectors 22 to one or more predetermined positions within the pivot range 108, and the detectors 22 acquire images at each of the one or more positions. Although the example is illustrated in a single dimension, it should be understood that the effective field of view may be increased by pivoting the detectors 22 or collimators 28 in other directions.

The support member 108 may be commanded by a radius controller 102 to move the detectors 22 toward and away from a patient along arrow C. A distance 124 may thus be changed to increase or decrease the distance from the patient. The support member 108 may be piston driven, spring loaded, chain driven, or any other type of actuator. Alternatively, the support member 108 may be mounted on a portion (not shown) of the gantry, and thus the portion may also be driven in the direction of arrow C. The radius may be changed while acquiring data or between acquisitions, and may be used in combination with other motions. Anti-collision software and/or sensors (not shown) may also be used to ensure that the patient does not collide with the detectors 22.

Figure 16:
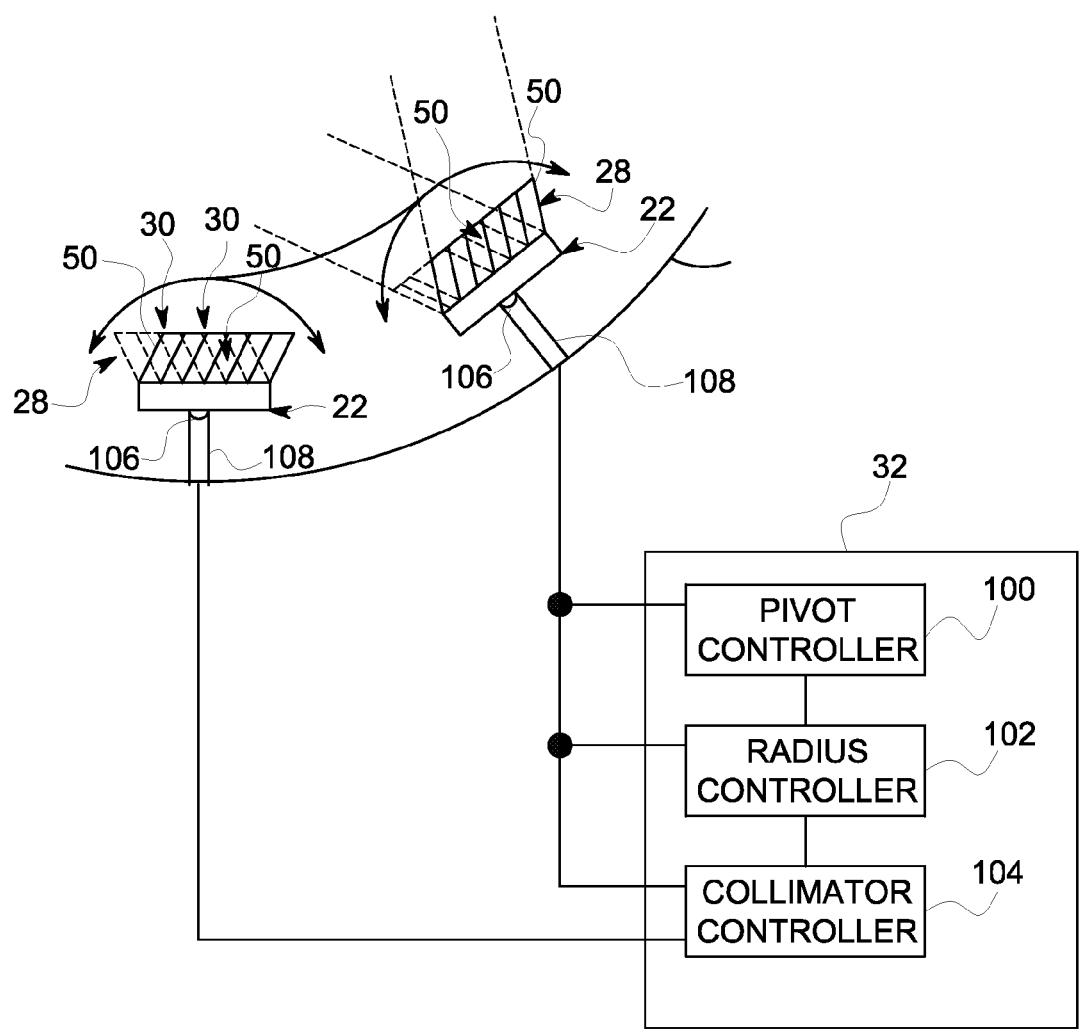
FIG. 16 is a diagram illustrating moving collimators formed in accordance with various embodiments.

In various embodiments, the adjustable collimators 28 are also provided as described herein and shown in FIG. 16. As illustrated, the radius controller 102 may move each of the detectors 22 closer to and further from a surface of the patient, and the pivot controller 100 may move the detectors 22 axially with respect to the patient 76. Additionally, in this embodiment, the collimator controller 104 may adjust a position of the adjustable collimator 28, which may be a collimator with adjustable segments 30 as described in more detail herein. By changing the geometry of the adjustable collimators 28, the effective FOV may be changed or increased to be greater than the actual FOV. In a configuration wherein the collimators 28 include a plurality of segments 30, the collimator controller 104 can move all or a sub-set of the segments 30 through a range of motion. The collimator controller 104 may move the segments 30 predetermined distances, stop, and then acquire an image before moving the segments 30 to a next imaging position. Alternatively, the collimator controller 104 may move the segments 30 in a smooth sweeping motion, acquiring a single image across the effective FOV.

Figure 17:
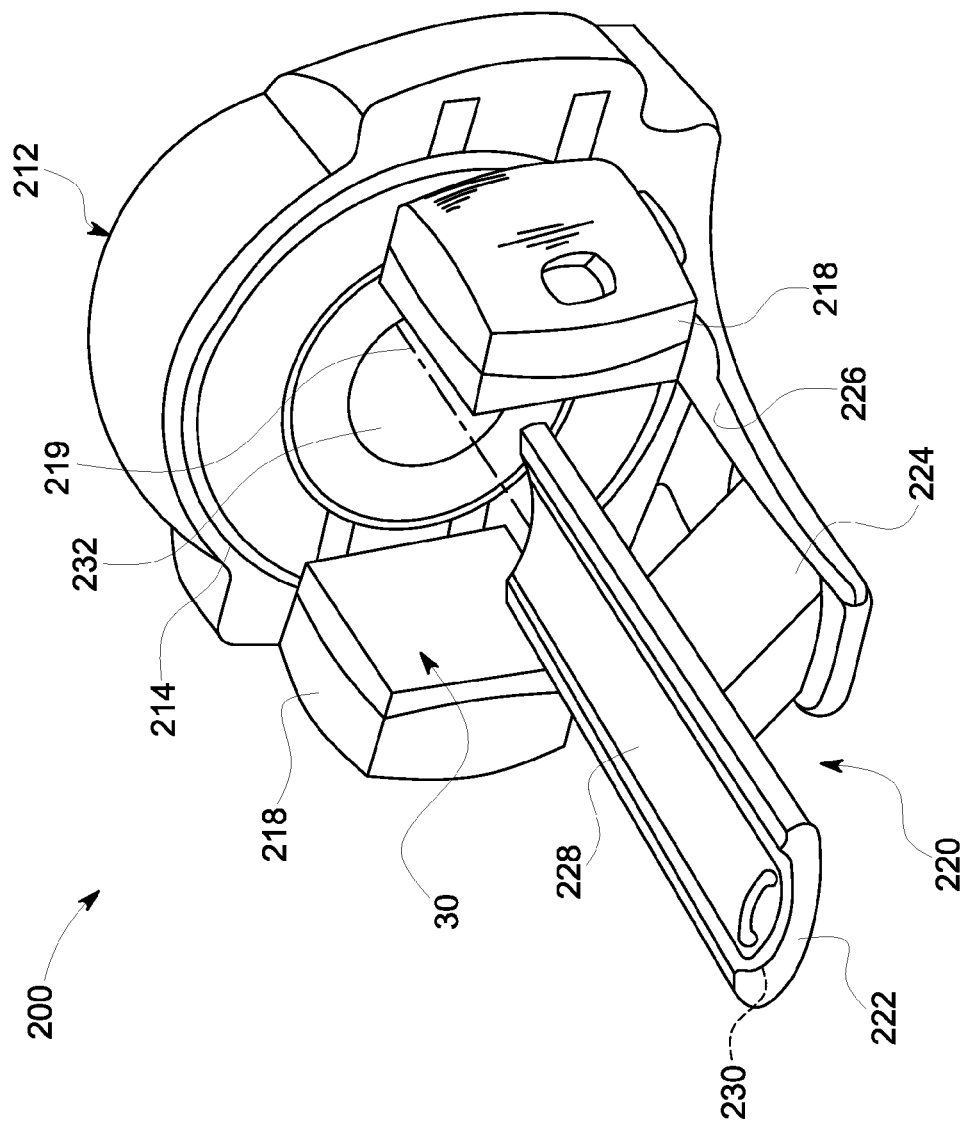
FIG. 17 is a perspective view of an exemplary NM imaging system formed in accordance with various embodiments.

The detectors 22 with adjustable collimators 28 of the various embodiments may be provided as part of different types of imaging systems, for example, NM imaging systems such as SPECT imaging systems having different detector configurations. For example, FIG. 17 is a perspective view of an exemplary embodiment of a medical imaging system 210 constructed in accordance with various embodiments, which in this embodiment is a SPECT imaging system. The system 210 includes an integrated gantry 212 that further includes a rotor 214 oriented about a gantry central bore 232. The rotor 214 is configured to support one or more NM cameras 218 (two cameras 218 are shown). The NM cameras 218 may be provided similar to the detectors 22 with the adjustable collimators 28. It should be noted that the detectors, for example, the detectors 22 or NM cameras 218 are generally equipped with interchangeable collimators. For example, the detector 22 or NM camera 218 is supplied with a plurality of collimators (or collimator pairs for a dual head cameras) wherein each collimator type is used for one type or a few different types of medical imaging procedures. According to some embodiments, at least one fixed-segment collimator is supplied with the detector 22 or NM camera 218 to be used for imaging an OOI having a size smaller than the entire FOV of the detector 22 or NM camera 218 when fitted with a standard parallel hole collimator. In other embodiments, a set of fixed-segment collimators is supplied with the detector 22 or NM camera 218. In still other embodiments, a plurality of different fixed-segment collimators or fixed-segment collimator sets is provided. In some embodiments, the fixed-segment collimator or collimators are used for applications where more expensive fan-beam or cone beam collimators can be used. In operation, in some embodiments, at least one of the standard collimators is replaced with a collimator according to one of the various embodiments.

In various embodiments, the cameras 218 may be formed from pixelated detectors or a single detector material (e.g., NaI). The rotors 214 are further configured to rotate axially about an examination axis 219.

A patient table 220 may include a bed 222 slidingly coupled to a bed support system 224, which may be coupled directly to a floor or may be coupled to the gantry 212 through a base 226 coupled to the gantry 212. The bed 222 may include a stretcher 228 slidingly coupled to an upper surface 230 of the bed 222. The patient table 220 is configured to facilitate ingress and egress of a patient (not shown) into an examination position that is substantially aligned with examination axis 219. During an imaging scan, the patient table 220 may be controlled to move the bed 222 and/or stretcher 228 axially into and out of a bore 232. The operation and control of the imaging system 200 may be performed in any suitable manner. It should be noted that the various embodiments may be implemented in connection with imaging systems that include rotating gantries or stationary gantries.

Thus, various embodiments provide synthetic fanbeam or adaptive fanbeam collimation that allows adjustment of both the location and size of the FOV of an imaging detector.

Figure 18:
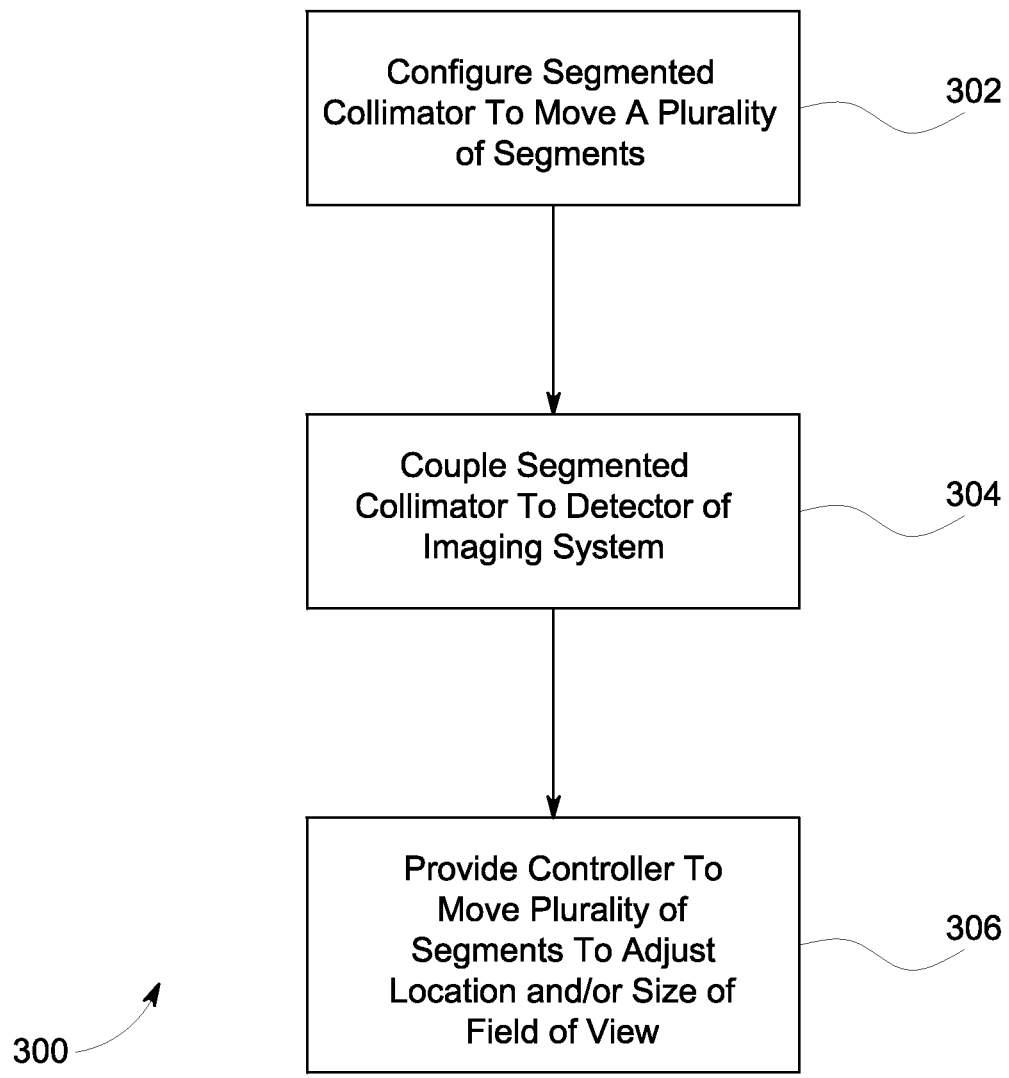
FIG. 18 is a flowchart of a method in accordance with various embodiments for collimating a detector of an imaging system.

Additionally, various embodiments provide a method 300 as illustrated in FIG. 18 for collimating a detector of an imaging system, such as an NM imaging system. The method 300 includes configuring at 302 a segmented collimator to move a plurality segments (independently or in groups) such that, for example, synthetic or adaptive fanbeam collimation is provided. In particular, a plurality of segments of a collimator is configured to move as described in more detail herein. For example, each of the segments may pivot or swivel about a pivot axis, with the pivot axis for each of the plurality of segments being parallel.

Thereafter, the segmented collimator is coupled to an imaging detector of an imaging system at 304. For example, the segmented collimator may be coupled to a front surface of one or more NaI SPECT gamma cameras. With the segmented collimator coupled to the imaging detector, a controller is provided at 306 to move the plurality of segments to adjust a location and/or size of the detector FOV. The movement may also include movement of the detector as described herein.

The control of the movement of the segmented collimator may be based on different types of information, such as a priori information or current scan acquisition information. Additionally, this information may be used to control other components of the imaging system, such as movement of the imaging detector (e.g., rotation of the imaging detector or tilting of the imaging detector) or movement of the patient table.

In various embodiments, the control of movement may be based on a priori information to determine or define a scan pattern for scanning an ROI or OOI. For example, prior information about general anatomy for a particular organ, the specific anatomy of a patient, prior scan data for the patient, or other data, may be used to determine or define movement of the segmented collimator. The movement may include a defined scan pattern based on the prior information such that an optimized scan of a particular organ is performed.

Additionally the control of movement may be based on current scan acquisition information, such that movement is controlled on-the-fly. In various embodiments, based on acquired scan data, which may include determining the location of an OOI after an initial scanning period, the movement of the segmented collimator, such as the defined scan pattern, may be changed to optimize scanning for the OOI of the patient. For example, adjustments in the scan pattern may be made based on acquired raw data counts (e.g., emission photon counts) or an initial image reconstruction to provide for the same number of counts to be acquired from each scan angle, a predetermined amount of counts (e.g., 80% of the counts) to be acquired from an OOI determined from the initial image reconstruction, or other desired or required imaging or scanning characteristics or operating parameters.

It should be noted that providing the controller may include providing hardware, software or a combination thereof to control the segmented collimator. The hardware and/or software may be integrated as part of the imaging system or provided separately therefrom, for example, as part of an upgrade installation. In other embodiments, an assembly is provided such that the assembly may be mounted or unmounted from the imaging system such that all of the parts (e.g., motors, segments, etc.) can be attached to the front of the imaging cameras and removed when not needed. Accordingly, a collimator assembly formed in accordance with various embodiments may be installed and removed from the imaging system.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A collimator for a radiation imaging detector, the collimator comprising:
    a plurality of adjustable segments;
    a plurality of collimator holes within each of the plurality of adjustable segments, and wherein the plurality of adjustable segments are configured to move independently of a detector to adjust a field of view of the collimator holes; and
    a shielding member between each of the plurality of adjustable segments.

2. The collimator of claim 1, wherein the plurality of adjustable segments are configured for swiveling about an axis parallel to an axis of rotation about a patient.

3. The collimator of claim 1, wherein the plurality of adjustable segments are independently movable from each of the other plurality of adjustable segments.

4. The collimator of claim 1, wherein at least two of the plurality of segments include collimator holes slanted at different angles.

5. The collimator of claim 1, wherein the plurality of adjustable segments pivot.

6. The collimator of claim 5, wherein at least one of the plurality of adjustable segments is pivoted at an angle different than the angle of at least one of the other plurality of adjustable segments.

7. The collimator of claim 1, wherein each of the plurality of adjustable segments includes a curved end and wherein the shielding member includes a complementary curved portion.

8. The collimator of claim 1, wherein the plurality of collimator holes are pre-slanted.

9. The collimator of claim 1, wherein the plurality of adjustable segments include collimator holes having different lengths.

10. A nuclear medicine (NM) imaging system comprising:
    a gantry;
    at least one imaging detector supported on the gantry and configured to rotate about the gantry defining an axis of rotation;
    a segmented collimator connected to the at least one imaging detector, the segmented collimator having a plurality of movable segments configured to move independently of the at least one imaging detector, wherein the movable segments are independently controllable;
    a controller configured to control movement of the movable segments; and
    an image reconstruction module configured to reconstruct an image from data acquired from the at least one imaging detector, wherein the image reconstruction module is configured to compute a probability that image voxels are obtained from a projection for a plurality of at least one of segments, detector or gantry angle combinations.

11. The NM imaging system of claim 10, wherein the plurality of movable segments are configured to swivel about an axis parallel to the axis of rotation.

12. The NM imaging system of claim 10, wherein the at least one imaging detector is pivotally connected to the gantry and configured for movement independent from the movement of the plurality of segments.

13. The NM imaging system of claim 10, wherein at least two of the plurality of segments are positioned at different swivel angles for imaging.

14. The NM imaging system of claim 10, wherein the at least one imaging detector comprises a Single Photon Emission Computed Tomography (SPECT) camera.

15. The NM imaging system of claim 10, wherein the plurality of segments are configured for sweeping operating at each of a plurality of positions of the at least one imaging detector.

16. The NM imaging system of claim 10, wherein the collimator comprises pre-slanted holes.

17. A method for collimating a detector of an imaging system, the method comprising:
    configuring a segmented collimator to provide movement of each of a plurality of segments independently of a detector to adjust a field of view of collimator holes of the plurality of segments;
    coupling the segmented collimator to the detector of the imaging system; and
    providing a controller to control the imaging system to move at least one of the plurality of segments, the detector or a gantry of the imaging system to which the detector is coupled, wherein the controlling comprises using acquired scan acquisition information for a current scan to control movement of the segmented collimator.

18. The method of claim 17, wherein the controlling comprises one of swiveling the plurality of segments, pivoting the detector or rotating the detector about the gantry.

19. The method of claim 17, wherein the controlling comprises using at least one of (i) anatomical information or (ii) prior information for a patient to define a scan pattern to control movement of the segmented collimator.

20. The method of claim 17, wherein the controlling comprises changing a defined scan pattern based on the acquired scan information, wherein the acquired scan information comprises one of raw data counts or an initial image reconstruction.

* * * * *